(12) United States Patent
Kempe

(10) Patent No.: US 6,463,792 B2
(45) Date of Patent: Oct. 15, 2002

(54) PROBE DEVICE

(75) Inventor: Eberhard Kempe, Berlin (DE)

(73) Assignee: Biotechnologie Kempe GmbH (DE)

( * ) Notice: Subject to any disclaimer, the term of this patent is extended or adjusted under 35 U.S.C. 154(b) by 21 days.

(21) Appl. No.: 09/727,875

(22) Filed: Dec. 1, 2000

(30) Foreign Application Priority Data

Dec. 3, 1999 (DE) ......................................... 199 59 271

(51) Int. Cl.[7] ............................ G01N 25/00; G01N 7/12
(52) U.S. Cl. .................. 73/53.01; 73/64.56; 73/864.16; 73/864.21
(58) Field of Search ............................. 73/53.01, 23.33, 73/23.2, 64.56, 863.23, 864.16, 864.21

(56) References Cited

U.S. PATENT DOCUMENTS

| | | | | |
|---|---|---|---|---|
| 5,335,658 A | * | 8/1994 | Bedingham ................ | 128/632 |
| 5,347,851 A | * | 9/1994 | Grudzien, Jr. et al. ...... | 73/53.01 |
| 5,369,981 A | * | 12/1994 | Merz et al. ................ | 73/28.01 |
| 5,528,923 A | * | 6/1996 | Ledez et al. ............... | 73/19.12 |
| 5,553,484 A | * | 9/1996 | Bender et al. ............. | 73/53.01 |
| 5,979,219 A | * | 11/1999 | Sellmer-Wilsberg et al. .................... | 73/19.12 |
| 6,257,052 B1 | * | 7/2001 | Zelechonok ............... | 73/61.56 |

* cited by examiner

Primary Examiner—Hezron Williams
Assistant Examiner—David J. Wiggins
(74) Attorney, Agent, or Firm—McGlew and Tuttle, P.C.

(57) ABSTRACT

The invention relates to a probe device for determining the concentration of highly volatile components in liquids and/or gases, with a probe body (1) comprising a probe core (2) and a probe finger (3) being permeable for the highly volatile components, in the area of probe core (2) or of probe finger (3) a sensor (4) for the highly volatile components being provided, and comprising a protective tube (5) enclosing probe finger (3) and having passage openings (7). The invention teaches that protective tube (5) is configured as a piston (5) of a sluice device (6) having a measuring position and a servicing position of piston (5), and that passage openings (7) of piston (5) are disposed such that piston (5) has in addition the function of a slider valve sleeve, with probe finger (3) being connected over passage openings (7) in the measuring position to a measuring space (8) and in the servicing position to a servicing space (9) separated from measuring space (8).

20 Claims, 3 Drawing Sheets

PROBE DEVICE

FIELD OF THE INVENTION

The invention relates to a probe device for determining the concentration of highly volatile components in liquids and/or gases, with a probe body comprising a probe core and a probe finger being permeable for the highly volatile components, in the area of the probe core or of the probe finger a sensor for the highly volatile components being provided, and comprising a protective tube enclosing the probe finger and having passage openings. Such probe devices are particularly used in the fields of process supervision and/or process control of chemical and bio-technological processes. The concentration of one or several highly volatile components in a reaction space is measured, and the process is controlled and/or regulated according to the determined concentrations. Highly volatile components are substances the boiling points of which are typically lower than that of water. Examples for such substances are C1 to C8 hydrocarbons, C1 to C6 alkyl monoalcohols, C1 to C6 alkyl aldehydes, C1 to C6 alkyl ketones. C1 to C6 alkyl carboxyl acids, benzole, alkyl-substituted benzole, phenols etc. Oxidizable highly volatile compositions are in particular measurable. The sensor is sealed against the environment, and highly volatile components have access to the sensor over the permeable probe finger only. Sensors are for instance commercially available semi-conductor detectors and the like. The permeability of the probe finger is established by that over the probe finger having cutouts a suitable permeable material covering said cutouts is provided. Such permeable material is typically configured as a permeation membrane, and with regard to the material selection, an adjustment to the highly volatile component to be measured is easily made by the average man skilled in the art. The protective tube serves for the protection of such a permeation membrane from mechanical damage.

BACKGROUND OF THE INVENTION

A probe of the construction mentioned above is for instance known in the art from document EP 0 174 417 B1. The insofar prior art probe has proven excellent. It has been shown, however, that this probe can be improved in terms of handling. In the prior art probe, fixing in a flange of a reaction vessel takes usually place by means of for instance a cap screw, with the probe finger extending into a reaction space. It is disadvantageous herein that for cleaning or maintenance operations at the probe and/or the probe finger, the whole probe has to be removed by hand, which is very time consuming. Further it is disadvantageous that in the course of the disassembly (and the reassembly) of the probe the reaction vessel remains open for a certain period of time. This is disturbing particularly for bio-technical processes, since bio-technical processes are subject to special requirements with regard to sterility (safety against contamination of the reaction space by micro-organisms disturbing the process and/or internal environment.

SUMMARY AND OBJECTS OF THE INVENTION

Therefore, the invention is based on the technical problem to provide a probe for determining the concentration of highly volatile components, said probe being easily insertable into a reaction vessel and also easily removable therefrom and whereby in bio-technical processes a contamination of the reaction space for instance in the course of a probe finger cleaning operation is virtually excluded.

For solving this technical problem, the invention teaches that the protective tube is configured as a piston of a sluice device having a measuring position and a servicing position of the piston, and that passage openings of the piston are disposed such that the piston has in addition the function of a slider valve sleeve, with the probe finger being connected over the passage openings in the measuring position to a measuring space and in the servicing position to a servicing space separated from the measuring space. As a piston is designated a structure that can slide forwards and backwards in cylindrical guiding surfaces, with external sealing surfaces. The measuring space is normally formed by the reaction space of a process. Sideways to the measuring space is connected a servicing space to be sealed in a gas-tight manner. By an embodiment of the invention, the protective tube obtains two functions. On one hand, a function as a piston is established, and on the other hand, as a slider valve sleeve. The protective tube is thus simultaneously a slider valve sleeve and a drive element therefor. As a result it is achieved that by means of the protective tube, the probe finger can be brought in connection alternatively with the measuring space and the servicing space. It is understood that the servicing space can in turn be operated such that a contamination cannot take place. In practical applications, service of the probe is made as follows. During measurement, the protective tube connects the measuring space through the passage openings to the probe finger, and simultaneously separates the measuring space from the servicing space in a gas-tight manner. By forward drive of the protective tube configured as a piston, a displacement of the protective tube will take place, the probe finger being separated from the measuring space and connected to the servicing space. In the servicing position, the measuring space and the servicing space are hermetically sealed against each other. The servicing space typically permits access and discharge of (sterile) cleaning agents and the like. After service, the process is reversed, as described above, and the probe now after service is again connected to the measuring space.

It is achieved, by the invention, that the measuring space will in the course of maintenance of the probe or reassembly of the probe not at any time come into contact with a contaminated environment. Further, maintenance of the probe finger can be made without a time-consuming removal of the probe.

In a preferred embodiment of the invention, the sluice device is pneumatically operable, a cylindrical space being provided where the piston including a piston ring is slidable forwards and backwards between the measuring position and the servicing position by alternating pressure application on different sides of the piston ring. Such pneumatically operable sluice devices are per se known in the art from practical applications in conjunction with pH probes. Basically, however, other drive systems, such as electro-magnetic and/or electro-motoric, are also possible, then in the area of the probe and/or of the piston suitable mechanical drive elements having to be provided, such as spindle gears.

It is recommended that the servicing space comprises at least one part for rinsing fluids. Rinsing fluids may for instance be liquids or gases. Sterilized water may be used, if necessary with usual additions for cleaning. Moreover, corresponding to the process to take place in the measuring space, various rinsing fluids are possible. Care should only be taken that a rinsing fluid will not affect for chemical or bio-chemical reasons the process taking place in the measuring space, since during the displacement of the protective tube between the measuring position and the servicing position a connection between measuring space and servicing space will exist for a short time. Typically, the servicing space will comprise two ports for handling the rinsing fluids, a feeding port and a discharging port.

An advantageous embodiment with regard to the constructional configuration is characterized by that the piston carries the piston ring at the end directed away from the measuring space and/or that the probe core and the piston are connected by a screw connection in the area of the piston ring. It is recommended that the probe core extends immediately adjacent to the piston ring by at least one piston stroke length L and carries outside at least on one piston stroke length L a probe sealing face. The piston may carry at its end directed towards the measuring space a piston bottom sealing in the servicing position the measuring space in a gas-tight manner against the servicing space. Further, the piston may carry in the area directed towards the measuring space a piston sealing face, by means of which the servicing space is sealed in the servicing as well as measuring positions in a gas-tight manner against the cylindrical space and by means of which the measuring space is sealed in the measuring position in a gas-tight manner against the servicing space. As a result, by combination of the constructional features described above, an embodiment is provided, wherein the piston with assigned sealing elements of the servicing space will seal the latter against the environment. The cylindrical space in turn is sealed at its end directed towards the measuring space against the piston, and at its end directed away from the measuring space against the probe core.

The passage openings in the piston can basically be executed in an arbitrary manner. With regard to a long life of the sealing elements, it is recommended to adapt the passage openings as slots extending in the longitudinal direction of the piston between the piston bottom and the piston sealing face. The pneumatic operation can be performed with any usual pneumatic fluids, an operation by pressurized air (2 to 10 bars, preferably 3 to 5 bars) being preferred.

BRIEF DESCRIPTION OF THE DRAWINGS

In the following, the invention will be described in more detail by reference to drawings showing one embodiment only. There are.

DESCRIPTION OF THE PREFERRED EMBODIMENTS

Figure 1:
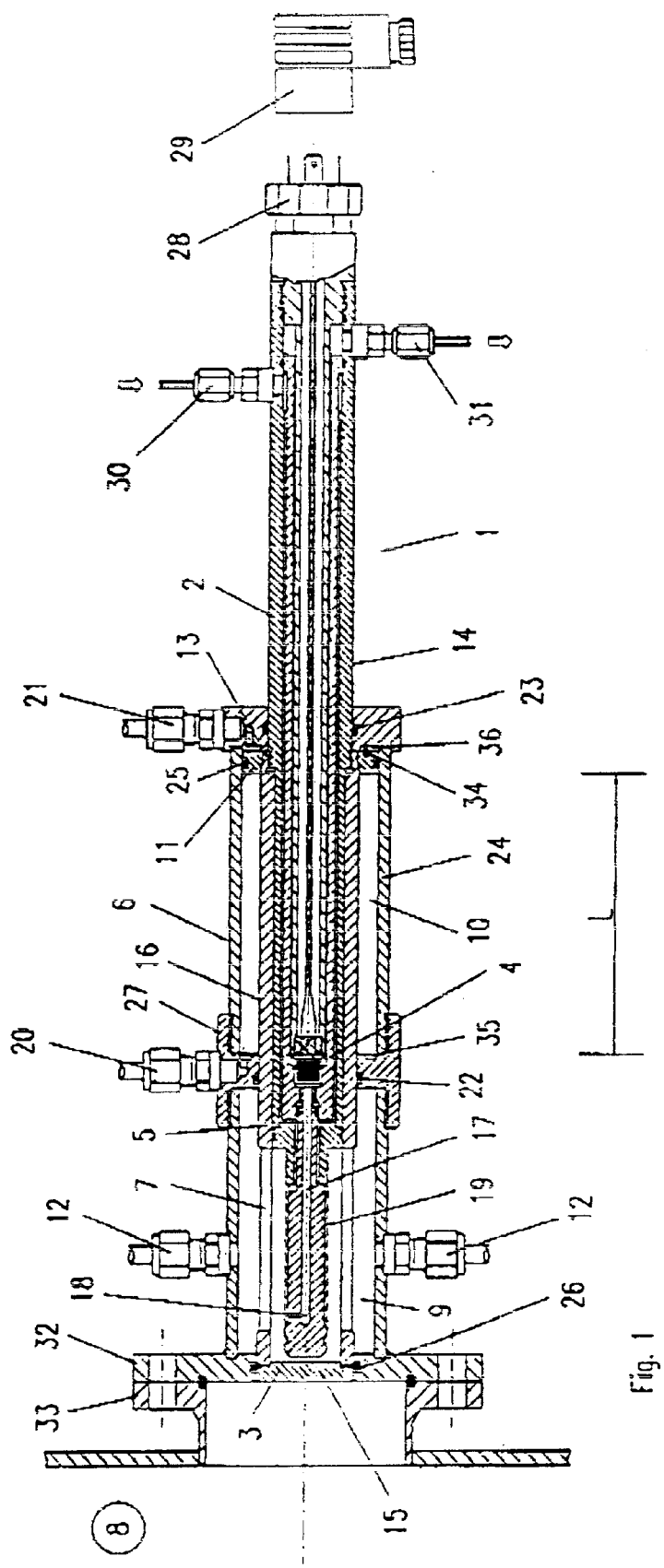
FIG. 1 a probe device according to the invention in a servicing position.
Figure 2:
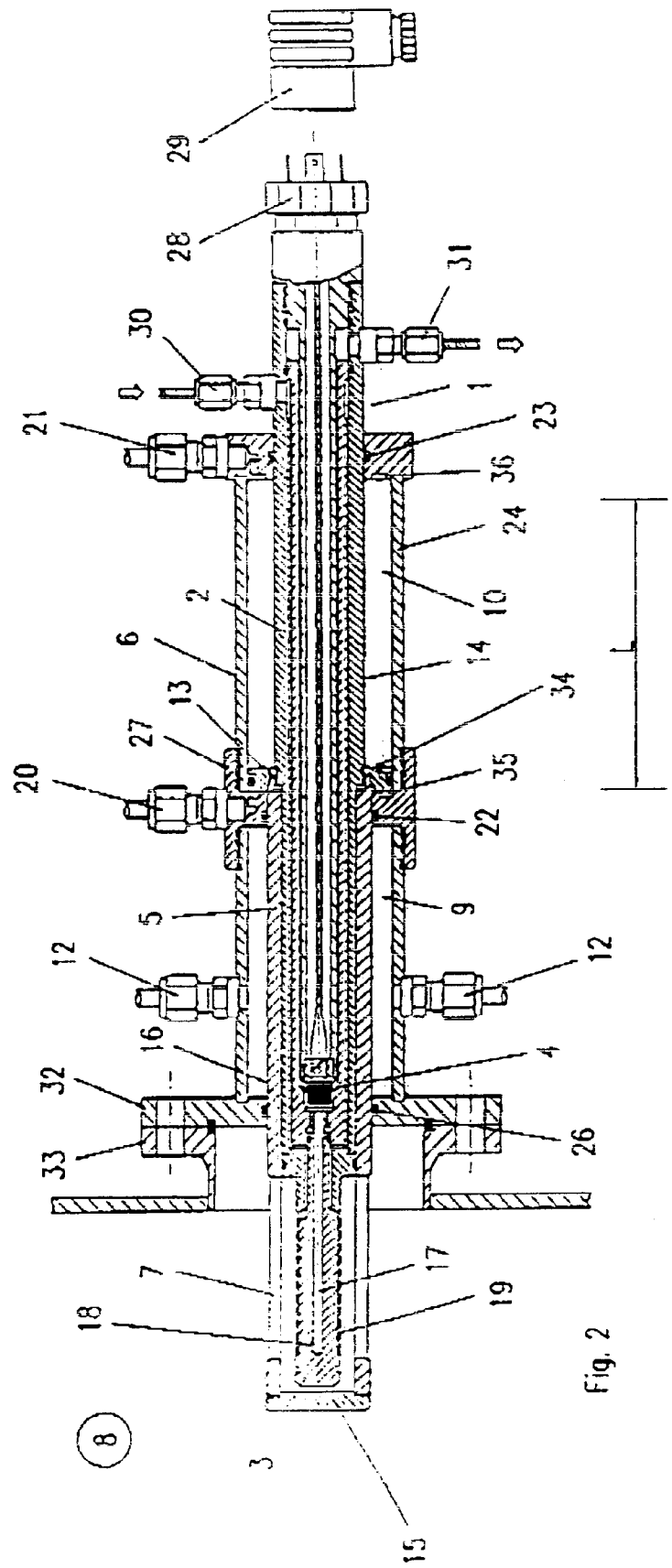
FIG. 2 the subject matter of FIG. 1, however in a measuring position.

In FIGS. 1 and 2 can be seen a probe device serving for the determination of C1 to C3 alkyl alcohols in a biotechnical process, namely a fermentation process. The probe device comprises a probe body 1 with a probe core 2 and a probe finger 3 being permeable for the highly volatile components. In the area of the probe core 2 is provided a sensor 4 for the highly volatile component, in this embodiment a $SnO_x$ detector. The detector is connected over a central channel 17 provided in probe finger 3 with a radially extending access borehole 18 to the inner side of a permeation membrane 19. The opposite side of permeation membrane 19 is provided with a protective tube 5 [or piston, equivalently] surrounding probe finger 3 and having passage openings 7, for the protection against mechanical damage. Moreover, channels for a carrier gas are provided, said channels having feeding and discharging ports 30, 31 for carrier gas and not being shown here in detail, for clarity reasons.

It can be further seen that the protective tube is adapted as a (in the shown embodiment: one-piece) piston 5 of a sluice device 6. In the representation of FIG. 1, piston 5 or probe core 2, respectively, is in a servicing position. This can be seen from that passage openings 7 are in the area of servicing space 9. By displacement of piston 5 including sensor core 2 (in FIG. 1 towards left), piston 5 can be displaced from the servicing position to a measuring position shown in FIG. 2. The displacement corresponds to a piston stroke length L. Corresponding to FIG. 2, passage openings 7 are then located in the area of measuring space 8.

The sluice device is pneumatically operable by means of pressurized air, for which purpose a cylindrical space 10 is provided, where piston 5 including a piston ring 11 is slidable forwards and backwards between the measuring position and the servicing position by alternating pressure application on different sides of piston ring 11. Alternating pressure application is achieved by control air ports 20 and 21. Servicing space 9 comprises two ports 12 for rinsing fluids. One of ports 12 can be used as a feeding port and the other port 12 as a discharging port.

In the figures can be seen that piston 5 carries piston ring 11 at the end directed away from measuring space 8. Probe core 2 and piston 5 are connected by a screw connection in the area of piston ring 11. This screw connection 13 permits to screw probe core 2 with probe finger 3 out from piston 5, and to remove the probe device, without any further disassembly of the probe device and/or of the sluice device. Probe core 2 follows, with assembled probe device, immediately to the piston ring and extends by at least one piston stroke length L beyond the latter. Probe core 2 comprises at the outside at lest on one piston stroke length L a probe sealing face 14. It is understood that the outside diameter of screw connection 13 is smaller than or equal to the outside diameter of sealing face 14. Cylindrical space 10 thus is separated from the environment by means of sealing element 22 acting between piston 5 and cylinder 24 and by means of sealing element 23 acting between cylinder 24 and sealing face 14. Piston ring 11 is sealed against cylinder 24 by sealing element 25. In the shown embodiment, sealing elements 22, 23 and 25 are configured as "O" rings from a rubber-elastic material being resistant against the employed media and substances. The same applies to the other sealing elements described below.

Piston 5 carries at its end directed towards measuring space 8 a piston bottom 15 sealing in the servicing position measuring space 8 in a gas-tight manner against servicing space 9. For this purpose, sealing element 26 is provided. Sealing of the servicing space against the environment and against measuring space 8 thus take place by means of the two sealing elements 22 and 26 acting against piston 5. For this purpose, piston 5 carries in the area directed towards measuring space 8 a piston sealing face 16, by means of which servicing space 9 is sealed in the servicing as well as measuring positions in a gas-tight manner against cylindrical space 10 and by means of which measuring space 8 is sealed in the measuring position in a gas-tight manner against servicing space 9. Passage openings 7 are adapted as slots extending in the longitudinal direction of the piston between piston bottom 5 and piston sealing face 16.

Further it can be seen that cylinder 24 is reversibly separable in its central position, namely between cylindrical space 10 and servicing space 9. For this purpose, connection element 27 is provided, into which two sections of cylinder 24 can sealingly be screwed in.

Finally, in FIGS. 1 and 2 can be seen an electrical terminal 28, with respective plug 29 for contacting sensor 4 and feeding and discharging ports 30, 31 for carrier gas. In the shown embodiment, a so-called carrier gas probe is used permitting relatively short response times. Sluice device 6 comprises a measurement connection such as connection flange 32 allowing connection to a corresponding connection flange 33 of measuring space 8.

Figures 3A, 3B:
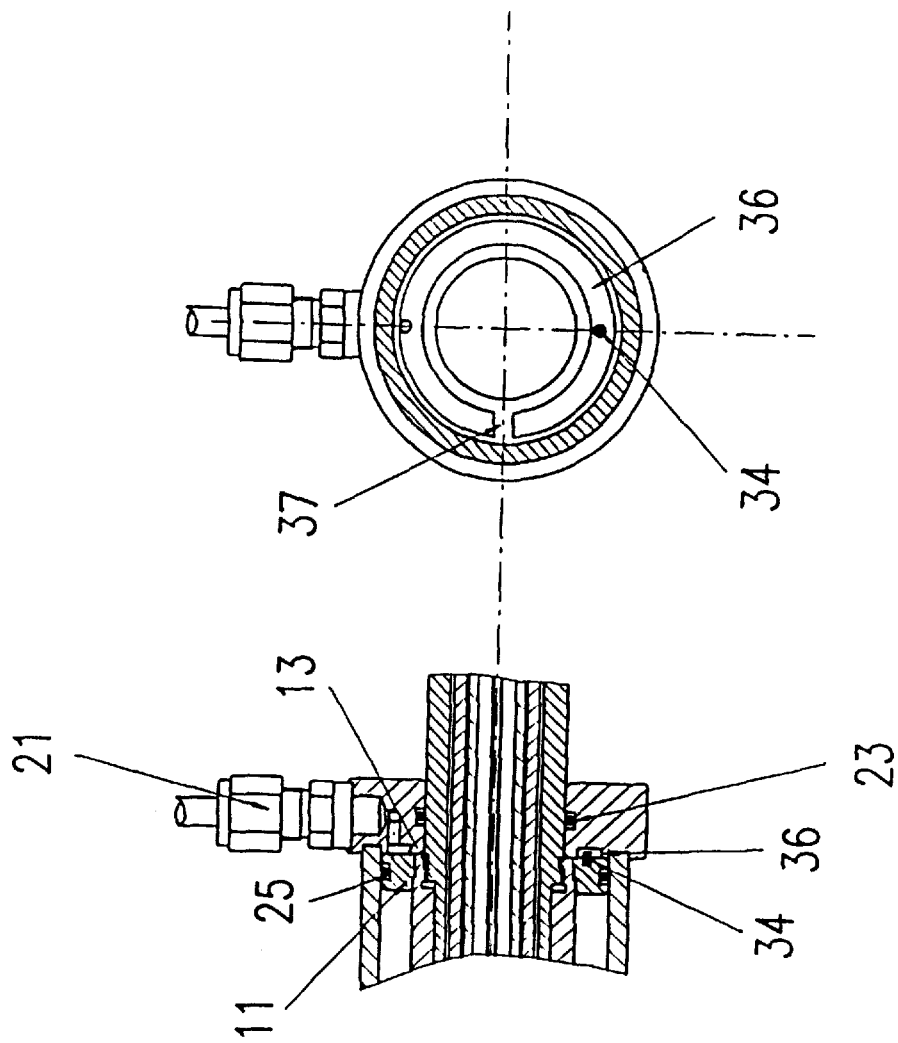
FIGS. 3a, 3b a detail view of the probe device in two different views.

In FIG. 3 is shown a special detail fulfilling a double function. In the representation can be seen that an inner front face of cylindrical space 10 comprises an annular groove 36 extending in a circular manner in the front face and being opposed to piston ring 11. The annular groove comprises an interruption web 37. In the shown servicing position, an element 34 preventing rotation (a pin) engages into annular groove 36. It is preferred that in the opposite front face of cylindrical space 10 a corresponding annular groove 35 (see FIGS. 1 and 2) and at the piston ring opposite a corresponding element preventing rotation are provided, since then the same functions can be obtained for the measuring position, too, as will be explained below.

On one hand, the annular groove secures that a sufficiently large portion of the surface of piston ring 11 opposite to the annular groove is subjected to the pressurized air, at the occasion of actuation. Thereby, a smooth movement of the piston ring being in an end position is achieved, when pressurized air is applied. The interruption web 37, in turn, causes in conjunction with element 34 preventing rotation that screw connection 13 can be released and connected, since during release of connection, element 34 preventing rotation will hit against the interruption web and thus secures piston 5 against further rotation.

What is claimed is:

1. A probe device for determining the concentration of highly volatile components in liquids and or gases, the probe comprising:
   a probe body with a probe core and a probe finger which is permeable for the highly volatile components;
   a sensor in the area of said probe core or in the area of said probe finger, said sensor sensing highly volatile components, said sensor comprising a protective tube enclosing said probe finger, said protective tube having passage openings, said protective tube being configured as a piston of a sluice device having a piston measuring position and a piston servicing position said passage openings of piston are disposed such that said piston has in addition the function of a slider valve sleeve, said probe finger being connected over said passage openings in the measuring position to a measuring space, and said probe finger being connected over said passage openings in the servicing position to a servicing space separated from the measuring space.

2. A probe device according to claim 1, wherein said sluice device is pneumatically operable, a cylindrical space being provided where said piston, including a piston ring is slidable forwards and backwards between the measuring position and the servicing position by alternating pressure application on different sides of said piston ring.

3. A probe device according to claim 1, wherein said servicing space comprises at least one port for admitting rinsing fluids.

4. A probe device according to claim 1, wherein said piston carries a piston ring at an end directed away from said measuring space.

5. A probe device according to claims 4, wherein said probe core and said piston are connected by a screw connection in an area of said piston ring.

6. A probe device according to claim 1, wherein said probe core extends immediately adjacent to said piston ring by at least one piston stroke length and carries outside a probe sealing face at least on one piston stroke length.

7. A probe device according to claim 1, wherein said piston carries, at its end directed towards said measuring space, a piston bottom, said piston bottom sealing said measuring space in a gas tight manner in the servicing position against said servicing space.

8. A probe device according to claim 1, wherein said piston carries in the area directed towards said measuring space a piston sealing face, said piston sealing face for sealing said servicing space in the servicing position and in the measuring position in a gas-tight manner against the cylindrical space and for sealing said measuring space in the measuring position in a gas-tight manner against said servicing space.

9. A probe device according to claim 1, wherein said passage openings are adapted as slots extending in a longitudinal direction of the piston between a bottom of said piston and said piston sealing face.

10. A probe device according to claim 1, wherein the device may be pneumatically operated with pressurized air.

11. A probe device for a vessel, the device comprising:
    a measurement connection connectable to the vessel and separating a measuring space inside the vessel from a servicing space outside the vessel;
    a piston movably connected through said measurement connection between a measuring position and a servicing position;
    a sensor arranged in said piston, said piston defining a passage for said sensor to communicate with an area outside said piston, said passage being arranged in said piston to communicate with said measuring space in said measuring position of said piston, said passage also being arranged in said piston to communicate with said servicing space in said servicing position of said piston.

12. A device in accordance with claim 11, wherein:
    said measurement connection seals with said piston to separate said measuring space from said servicing space in said measuring position and said servicing position.

13. A device in accordance with claim 12, further comprising:
    a cylinder connected to said measurement connection, said piston being movable in said cylinder, said servicing space being arranged between said cylinder and said piston,
    a cylinder seal sealing between said cylinder and said piston, said cylinder seal constantly sealing said servicing space from an area outside said servicing space and said measuring space.

14. A device in accordance with claim 12, further comprising:
    a sensor connection between said sensor and said piston, said sensor connection being disconnectable from said piston in said servicing position while said measurement connection seals with said piston;
    a permeable membrane in said passage and permeable to volatile components, said sensor sensing said volatile components.

15. A probe device according to claim 11, wherein said piston is pneumatically operable, a cylindrical space being provided between said piston and said cylinder, including a piston ring slidable forwards and backwards between the measuring position and the servicing position by alternating pressure application on different sides of said piston ring.

16. A probe device according to claim 11, wherein said servicing space comprises at least one port for rinsing fluids.

17. A probe device according to claim 11, wherein said piston carries a piston ring at an end directed away from said measuring space, said sensor and said piston being connected by a screw connection in an area of said piston ring.

18. A probe device according to claim 11, wherein said piston carries, at an end directed towards said measuring space, a piston bottom, said piston bottom sealing said measuring space in a gas tight manner in said servicing position against said servicing space.

19. A probe device according to claim 15, wherein said piston carries in the area directed towards said measuring space a piston sealing face, said piston sealing face sealing said servicing space in the servicing position and in the measuring position in a gas-tight manner against the cylindrical space and for sealing said measuring space in the measuring position in a gas-tight manner against said servicing space.

20. A probe device according to claim 18, wherein said passage is adapted as slots extending in a longitudinal direction of the piston between a bottom of said piston and said piston sealing face.

* * * * *